United States Patent [19]

Pauluth et al.

[11] Patent Number: 5,772,914
[45] Date of Patent: Jun. 30, 1998

[54] CHIRAL DOPES

[75] Inventors: Detlef Pauluth, Ober-Ramstadt; Matthias Bremer; Herbert Plach, both of Darmstadt; Georg Weber, Erzhausen, all of Germany

[73] Assignee: Merck Patent Gesellschaft mit Beschrankter Haftung, Darmstadt, Germany

[21] Appl. No.: 746,943

[22] Filed: Nov. 18, 1996

[30] Foreign Application Priority Data

Nov. 17, 1995 [DE] Germany ............... 195 42 849.8

[51] Int. Cl.⁶ ............ C09K 19/06; C09K 19/52; C09K 19/12; C07C 19/08
[52] U.S. Cl. ............ 252/299.6; 252/299.01; 252/299.61; 252/299.63; 252/299.64; 252/298.65; 252/299.66; 252/299.67; 568/626; 568/647; 548/136; 544/298; 549/369; 570/129
[58] Field of Search ............ 252/299.66, 299.6, 252/299.63, 299.01, 299.61, 299.65, 299.67, 299.64; 568/647, 626; 560/60, 65, 102; 548/136; 544/298; 570/129; 549/369

[56] References Cited

U.S. PATENT DOCUMENTS

| | | | |
|---|---|---|---|
| 5,290,477 | 3/1994 | Kondo et al. | 252/299.61 |
| 5,324,451 | 6/1994 | Takehara et al. | 252/299.65 |
| 5,356,563 | 10/1994 | Buchecker et al. | 252/299.63 |
| 5,486,310 | 1/1996 | Buchecker et al. | 252/299.61 |
| 5,494,605 | 2/1996 | Kurihara et al. | 252/299.66 |
| 5,611,957 | 3/1997 | McDonnell et al. | 252/299.01 |

*Primary Examiner*—C. H. Kelly
*Attorney, Agent, or Firm*—Millen, White, Zelano & Branigan, P.C.

[57] ABSTRACT

Chiral benzene derivatives of formula I

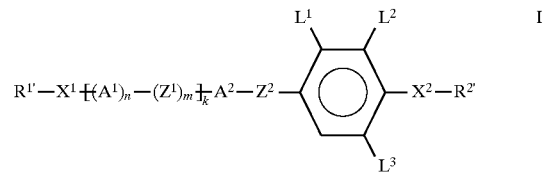

in which $R^{1*}$, $R^{2*}$, $X^1$, $X^2$, $A^1$, $A^2$, $Z^1$, $Z^2$, $L^1$, $L^2$, $L^3$, m, n and k are as defined in claim 1, and their use as chiral dopes in liquid-crystalline media, particularly for electrooptical displays, and to electrooptical displays containing such media.

19 Claims, No Drawings

CHIRAL DOPES

The invention relates to chiral benzene derivatives of the formula I

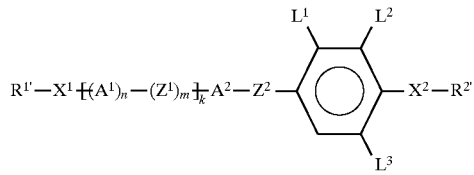

in which

L$^1$, L$^2$ and L$^3$ are each, independently of one another, F or H,

X$^1$ and X$^2$ are each, independently of one another, O or a single bond,

R$^{1*}$ and R$^{2*}$ are each, independently of one another, a chiral radical containing at least one alkyl chain preferably having 1 to 15 carbon atoms, in which one or more non-adjacent CH$_2$ groups may be replaced by O or CH=CH, A$^1$ and A$^2$ are each, independently of one another, 1,4-phenylene which is unsubstituted or substituted by one or two fluorine atoms and in which, in addition, one or two CH groups may be replaced by N, or unsubstituted 1,4-cyclohexylene in which, in addition, one or two CH$_2$ groups may be replaced by O or S, or thiadiazole-2,5-diyl or 1,4-bicyclo[2.2.2]octylene, Z$^1$ and Z$^2$ are each, independently of one another, —COO—, —OCO—, —OCH$_2$—, —CH$_2$O—, —CH$_2$CH$_2$—, —CH=CH—, —C≡C— or a single bond, k is 0, 1 or 2, and n and m are each, independently of one another, 0 or 1, with the proviso that, in the case where L$^1$, L$^2$ and L$^3$ are all simultaneously H, at least One of the groups R$^{1*}$ and R$^{2*}$ is a chiral radical in which at least one CH$_2$ group has been replaced by CH—CH.

Above and below,

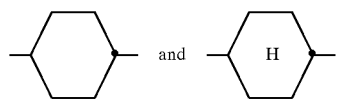

are 1,4-cyclohexylene, in which, in addition, one or two CH$_2$ groups may be replaced by O or S.

BACKGROUND OF THE INVENTION

Liquid crystals have in the last decade achieved entry into various technical areas in which electrooptical and display-device properties are desired (for example in watch, calculator and typewriter displays). These display devices are based on the dielectric alignment effects in the nematic, cholesteric and/or smectic phases of the liquid-crystalline compounds, where—caused by the dielectric anisotropy—the long molecular axes of the compounds adopt a preferential alignment in an applied electric field. The customary response times in these display devices are too long for many other potential areas of application of liquid crystals. This disadvantage is particularly noticeable if a large number of pixels must be addressed. The production costs of the equipment containing relatively large screen areas, such as, for example, of video equipment; are then generally too high.

In addition to nematic and cholesteric liquid crystals, optically active smectic liquid-crystal phases have also increased in importance over the last few years.

Clark and Lagerwall have been able to show that the use of ferroelectric liquid-crystal systems in very thin cells gives optoelectric switching or display elements which have response times faster by a factor of up to 1000 compared with conventional TN ("twisted nematic") cells (cf., for example, Lagerwall et al. "Ferroelectric Liquid Crystals for Displays", SID Symposium, October Meeting 1985, San Diego, Calif., U.S.A.). Owing to these and other favorable properties, for example the possibility of bistable switching and the virtually viewing-angle-independent contrast, FLCs are in principle highly suitable for the abovementioned areas of application, for example via matrix addressing.

Electro-optical switching and display elements either require compounds which form tilted or orthogonal smectic phases and are themselves optically active, or ferroelectric smectic phases can be induced by doping compounds which, although forming smectic phases, are not themselves optically active with optically active compounds. The desired phase should be stable over the broadest possible temperature range.

In order to achieve a good contrast ratio in electro-optical components, a uniform planar alignment for liquid crystals is required. Good alignment in the S$^*_A$ and S$^*_C$ phase can be achieved if the phase sequence of the liquid-crystal mixture is as follows, with decreasing temperature:

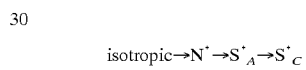

The prerequisite is that the pitch of the helix in the N$^*$ phase is very large (greater than 10 μm) or even better is fully compensated (see, for example, T. Matsumoto et al., p. 468–470, Proc. of the 6th int. Display Research Conf., Japan Display, Sept. 30–Oct. 2, 1986, Tokyo, Japan; N. Nurakami et al., ibid. p. 344–p. 347). This is achieved by adding a further optically active dope which induces a right-handed helix to the chiral liquid-crystal mixture which has, for example, a left-handed helix in the N$^*$ phase in such amounts that the helix is just compensated.

EP 0 304 738 describes chiral dopes containing two chiral side groups in which the two chiral terminal groups have the same absolute configuration. JP(A)M07-080 816 describes chiral compounds containing ester bridges and two saturated chiral terminal groups.

SUMMARY OF THE INVENTION

It has been found, in particular, that optically active benzene derivatives of the formula I as dopes in tilted smectic liquid-crystal phases result in a high degree of twist in the cholesteric phase even when added in small amounts.

This helix induced in the N$^*$ phase can advantageously be used in mixtures for specific compensation of the pitch. It is particularly advantageous here that the novel dopes compensate the pitch of another dope, even when added in small amounts, owing to their strong twisting power.

It has also been found that the optically active benzene derivatives of the formula I, as dopes in nematic liquid-crystal phases, result in a high degree of twist in the cholesteric phase even when added in small amounts.

The sole use of the novel dopes allows the preparation of mixtures having low temperature dependence of the pitch.

JP-2 157 248 discloses similar optically active 2,6-difluorobenzene derivatives. However, these contain an ester group and are unsuitable for helix compensation, since they have a very large pitch themselves. In addition, these compounds have a voltage holding ratio which is unsatisfactory for active matrix addressing (for example G. Weber et al., Liquid Crystals 5, 1381 (1989)).

The invention therefore relates to the chiral benzene derivatives of the formula I, in particular in which at least one the radicals $R^{1*}$ and $R^{2*}$ is a radical of the formula II

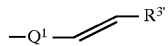
II in which
Q$^1$ is a single bond or an alkylene group preferably having 1 to 8 carbon atoms in which, in addition, one, two or more CH$_2$ groups may be replaced by —O— in such a way that two heteroatoms are not adjacent, and
$R^{3*}$ is a chiral radical.

Preference is given to radicals of the formula II which contain no conjugated double bonds.

Particular preference is given to compounds of the formula I in which $R^{1*}$ is a chiral radical of the formula II.

Preference is furthermore given to chiral derivatives of the formula I in which
$R^{2*}$ is a radical of the formula III

III in which
Q$^1$ and $R^{3*}$ are as defined above.

Particular preference is given to chiral derivatives in which $R^{3*}$ is a chiral radical of the formula IV

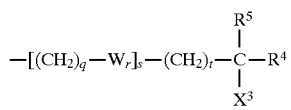
IV in which
W is CH=CH or O,

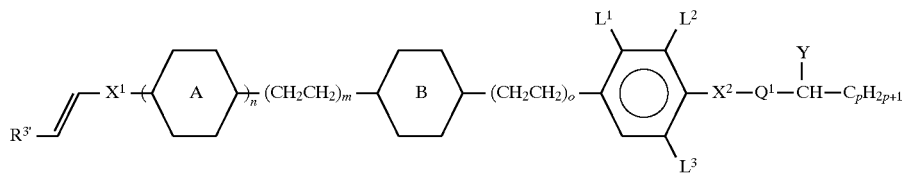

$X^3$ is H, CH$_3$, F, Cl, CF$_3$, CF$_2$H, CFH$_2$ or CN,
$R^4$ is an alkyl radical preferably having 1 to 8 carbon atoms which is different from $X^3$ and in which one, two or more CH$_2$ groups may be replaced by —O— and/or by CH=CH in such a way that no two O atoms are adjacent,
$R^5$ is an alkyl radical preferably having 1 to 8 carbon atoms which is different from $X^3$ and $R^4$ and in which one, two or more CH$_2$ groups may be replaced, independently of one another, by —O— and/or CH=CH in such a way that no two O atoms are adjacent,
s is from 0 to 4,
r is 0 or 1,
q is from 0 to 8, and
t is from 0 to 8, where the sum of q, r and t is from 0 to 16, preferably from 0 to 8.

Compounds of the formula I1 are particularly preferred:

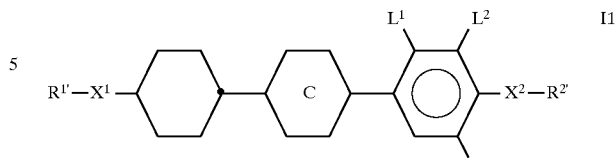

where

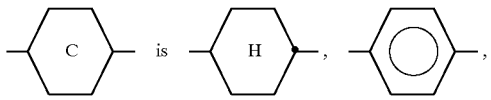

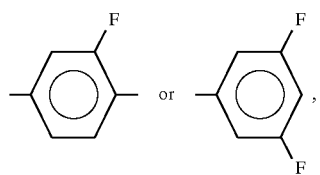

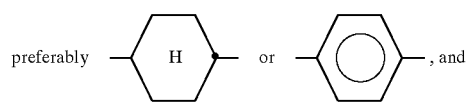

$R^{1*}$, $X^1$, $L^1$, $L^2$, $L^3$, $X^2$ and $R^{2*}$ are as defined above.

Particular preference is furthermore given to chiral derivatives of the formula I2

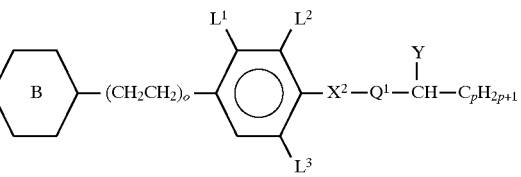

in which
$L^1$, $L^2$, $L^3$, $R^{3*}$, $X^1$, $X^2$ and $Q^1$ are as defined above, and
Y is CH$_3$, halogen, CF$_3$, CF$_2$H, CH$_2$F or CN,

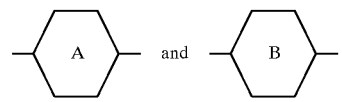

are each, independently of one another,

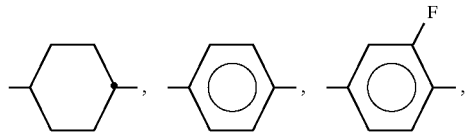

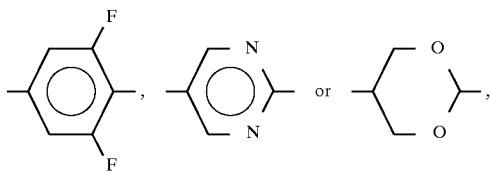

n, m and o are each, independently of one another, 0 or 1, and p is from 2 to 8.

Particular preference is given to compounds in which at least one of the radicals $L^2$ and $L^3$ is F. It is very particularly preferred for the two radicals $L^2$ and $L^3$ to be simultaneously F.

Preference is given to chiral compounds of the formula I2 in which

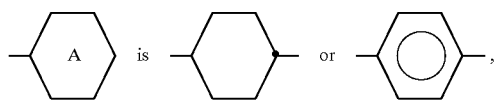

particularly preferably

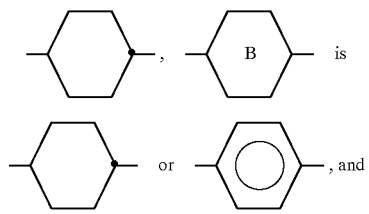

m+o is 0 or 1.

Particular preference is given to compounds of the formula I in which the two chiral groups $R^{1*}$ and $R^{2*}$ have the same absolute configuration, i.e., (S,S) or (R,R).

For active matrix (AM) applications, chiral compounds of the formula I which contain no ester groups are preferred.

The invention furthermore relates to liquid-crystalline media comprising at least two liquid-crystalline components, characterized in that they include at least one compound of the formula I. Particular preference is given here to compounds of the formula I which contain at least one structural unit of the formula II.

Preference is given to liquid-crystalline media which comprise one or more compounds of the formula I which contain no ester groups.

Very particular preference is given to liquid-crystalline media which comprise at least one compound of the formula I and have a temperature dependence of the cholesteric pitch of, preferably, less than 0.1%/° C. and particularly preferably of less than 0.05%/° C. in the range from T=0° C. to 50° C. Particular preference is given to media with temperature dependences of less than 0.02%/° C. Temperature dependences of between 0.001 and 0.05%/° C. are also preferred. The above-mentioned temperature dependences are numerical values. The temperature dependence of the pitch itself can be either positive or negative in accordance with the present invention.

The invention furthermore relates to electrooptical displays containing a liquid-crystalline medium as described above, in particular a supertwist (STN) liquid-crystal display or an active matrix liquid-crystal display having two plane-parallel outer plates which, together with a frame, form a cell, a nematic liquid-crystal mixture of positive dielectric anisotropy located in the cell, electrode layers with overlying alignment layers on the insides of the outer plates, a tilt angle between the long axis of the molecules at the surface of the outer plates and the outer plates of from about 1 degree to 30 degrees, and a twist angle of the liquid-crystal mixture in the cell from alignment layer to alignment layer with a value of from 60° to 600° for STN displays, preferably from 120° to 360°, and preferably from 70° to 110° for AM displays, where the nematic liquid-crystal mixture a) is based on component A consisting of one or more compounds having a dielectric anisotropy of from greater than +1.5 to +40, b) comprises 0–40% by weight of a liquid-crystalline component B consisting of one or more compounds having a dielectric anisotropy of from −1.5 to +1.5, c) comprises 0–20% by weight of a liquid-crystalline component C consisting of one or more compounds having a dielectric anisotropy of less than −1.5, and d) comprises an optically active component D in such an amount that the ratio between the layer thickness (separation between the plane-parallel outer plates) and the natural pitch of the chiral nematic liquid-crystal mixture is from about 0.2 to 1.3 in the case of the STN display and is from about 0.01 to 0.45 in the case of the AM display, and the optically active component D comprises at least one compound of the formula I, the nematic liquid-crystal mixture having a nematic phase range of at least 60° C., a viscosity at 20° C. of not greater than 35 mPa·s and a dielectric anisotropy of at least +1, where the dielectric anisotropies of the compounds and the parameters based on the nematic liquid-crystal mixture are based on a temperature of 20° C.

The liquid-crystal media for AM displays are preferably based on terminally fluorinated liquid-crystal compounds and the media for STN displays preferably include at least 10% of a cyano-substituted compound for component A. Media of this type preferably include less than 5% of compounds containing ester groups. For AM displays, the mixtures are particularly preferably based on compounds containing no ester groups. For many such applications, the media consist exclusively of compounds containing no ester groups.

The invention also relates to chiral tilted smectic liquid-crystalline media containing at least one compound of the formula I, in particular a ferroelectric liquid-crystalline medium comprising an achiral smectic component S which includes at least one achiral smectic liquid-crystalline compound, and a chiral component D which includes at least one chiral dope, where at least one chiral dope is a compound of formula I.

The invention furthermore relates to electrooptical display elements containing phases of this type, in particular liquid-crystal, switching and display devices containing a ferroelectric liquid-crystalline medium, outer plates, electrodes, at least one alignment layer and, if desired, additional auxiliary layers. The ferroelectric medium which includes at least one compound of the formula I preferably being a medium with a temperature dependence of the cholesteric pitch in the range of 0° to 50° C. of at most 0.1%/° C.

The invention furthermore relates to electrooptical display elements with active-matrix addressing which comprise nematic or cholesteric phases which include at least one compound of the formula I.

The term "containing no ester groups" means that the mesogenic group contains no carboxylate groups, —O—CO— and/or —CO—O—. Compounds of this type are particularly preferred as base material and as chiral compounds in AM displays.

Above and below, $L^1$, $L^2$, $L^3$, $R^{1*}$, $R^{2*}$, $R^{3*}$, $R^4$, $R^5$, $A^1$, $A^2$, $Q^1$, $X^1$, $X^2$, $X^3$, W, Y, $Z^1$, $Z^2$, k, m, n, o, p, q, r, s, t, u, v, w,

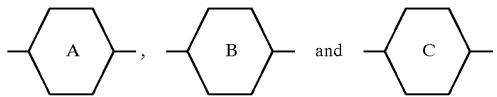

are as defined above, unless expressly stated otherwise.

Above and below, PhF denotes a 2-fluoro-1,4-phenylene group of the formula

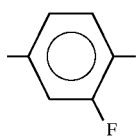

Above and below, PHFF denotes a 2,6-difluoro-1,4-phenylene group of the formula

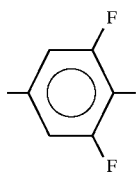

Accordingly, the compounds of the formula I include, in particular, compounds of the subformulae Ia to Ir:

$R^{1*}$-$X^1$-$A^2$-PhF-$X^2$-$R^{2*}$ Ia
$R^{1*}$-$X^1$-$A^2$-PhFF-$X^2$-$R^2$ Ib
$R^{1*}$-$X^1$-$A^2$-$Z^2$-PhF-$X^2$-$R^{2*}$ Ic
$R^{1*}$-$X^1$-$A^2$-$Z^2$-phFF-$X^2$-$R^{2*}$ Id
$R^{1*}$-$X^1$-$A^1$-$A^2$-PhF-$X^2$-$R^{2*}$ Ie
$R^{1*}$-$X^1$-$A^1$-$A^2$-PhFF-$X^2$-$R^{2*}$ If
$R^{1*}$-$X^1$-$A^1$-$A^2$-$Z^2$-PhF-$X^2$-$R^{2*}$ Ig
$R^{1*}$-$X^1$-$A^1$-$A^2$-$Z^2$-PhFF-$X^2$-$R^{2*}$ Ih
$R^{1*}$-$X^1$-$A^1$-$Z^1$-$A^2$-PhF-$X^2$-$R^{2*}$ Ii
$R^{1*}$-$X^1$-$A^1$-$Z^1$-$A^2$-PhFF-$X^2$-$R^{2*}$ Ij
$R^{1*}$-$A^1$-$Z^1$-$A^2$-$Z^2$-PhF-$X^2$-$R^{2*}$ Ik
$R^1$-$X^1$-$A^1$-$Z^1$-$A^2$-$Z^2$-PhFF-$X^2$-$R^{2*}$ Il
$R^{1*}$-$X^1$-$A^1$-$A^1$-$A^2$-PhF-$X^2$-$R^{2*}$ Im
$R^{1*}$-$X^1$-$A^1$-$A^1$-$A^2$-PhFf-$X^2$-$R^{2*}$ In
$R^{1*}$-$X^1$-$A^1$-$A^1$-$A^2$-$Z^2$-PhF-$X^2$-$R^{2*}$ Io
$R^{1*}$-$X^1$-$A^1$-$A^1$-$A^2$-$Z^2$-PhFF-$X^2$-$R^{2*}$ Ip
$R^{1*}$-$X^1$-$A^1$-$A^1$-$Z^1$-$A^2$-PhF-$X^2$-$R^{2*}$ Iq
$R^{1*}$-$X^1$-$A^1$-$A^1$-$Z^1$-$A^2$-PhFF-$X^2$-$R^{2*}$ Ir

Of these, those of the formulae Ia, Ib, Ic, Id, If, Ig and Ih are particularly preferred.

The branched groups $R^1$ of this type generally contain not more than two chain branches. $R^{1*}$ is preferably a branched group containing not more than one chain branch.

Preferred branched radicals are 2-butyl(=1-methylpropyl), 2-methylbutyl, 2-methylpentyl, 3-methylpentyl, 2-ethylhexyl, 2-methylbutoxy, 2-methylpentoxy, 3-methylpentoxy, 2-ethylhexoxy, 1-methylhexoxy and 1-methylheptoxy.

$R^{1*}$ and $R^{2*}$ are preferably alkyl or alkenyl having 1 to 15 carbon atoms. Particular preference is given to alkyl having 5 to 12 carbon atoms, i.e. pentyl, hexyl, heptyl, octyl, nonyl, decyl, undecyl, and dodecyl. $R^{2*}$ is preferably branched alkyl containing one branch.

At least one of the radicals $R^{1*}$ and $R^{2*}$ is preferably an alkenyl radical.

The formulae (1) to (3) are particularly preferred meanings of the chiral structural units $R^{1*}$ and/or $R^{2*}$:

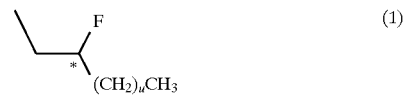

(1)

(2)

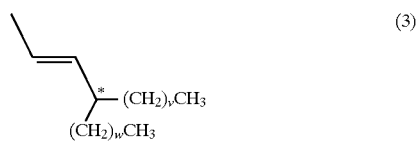

(3)

in which u, v and w are from 0 to 7, and v≠w. "*" denotes the chiral carbon atom.

Particular preference is given to compounds of the formula I and of the subformulae thereof in which the two chiral radicals $R^{1*}$ and $R^2$ have the same absolute configuration, e.g., (R,R) or (S,S).

$Z^1$ and $Z^2$ are preferably each, independently of one another, even when there are a plurality of groups $Z^1$, —CH$_2$CH$_2$—, —CH=CH—, —C≡C— or a single bond, particularly preferably a single bond.

k is preferably 0 or 1, n is preferably 1, and m is preferably 0.

The rings $A^1$ and $A^2$ preferably have one of the meanings 1–8 below:

1

2

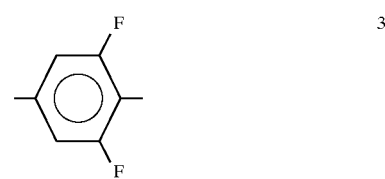

3

4

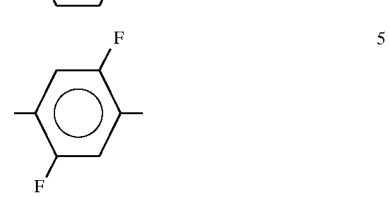

5

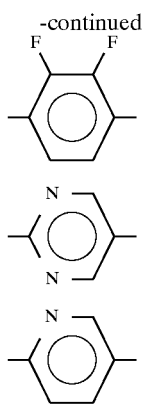

where the structural units (rings) can also be inverted.

The meanings 1, 2, 3, 4 and 6, in particular 1, 2 and 4, are particularly preferred.

Particular preference is given to compounds with meanings 1 and 2 for $A^1$ and $A^2$, where $Z^1$ and/or $Z^2$ are a single bond or —$C_2H_4$—.

Of these compounds of the formula I and of the subformulae, preference is given to those in which at least one of the radicals present therein has one of the preferred meanings indicated.

A very particularly preferred subgeneric group of compounds of the formula I consists of those of the subformulae I3 to I9:

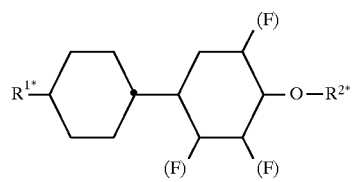

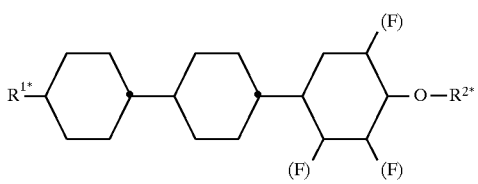

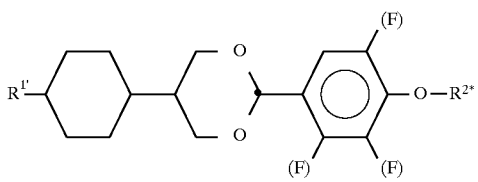

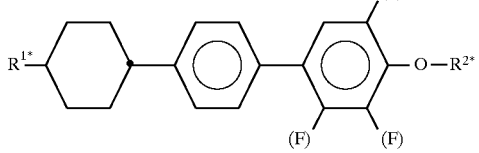

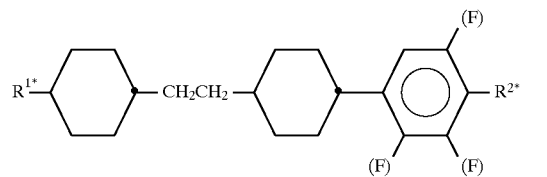

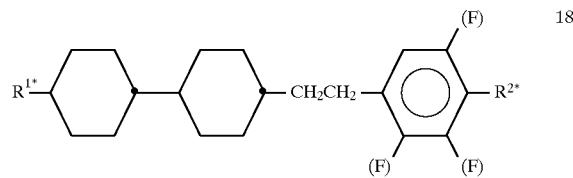

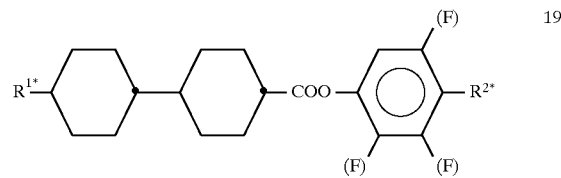

The compounds of the formula I are prepared by methods known per se, as described in the literature (for example in the standard works, such as Houben-Weyl, Methoden der organischen Chemie, Georg-Thieme-Verlag, Stuttgart), to be precise under reaction conditions which are known and suitable for the said reactions. Use can also be made here of variants which are known per se but are not mentioned here in great detail.

The compounds of the formula I in which $R^{1*}$ is a radical of the formula II, $X^1$ is a single bond and $X^2$ is O are prepared, for example, as shown in scheme 1:

Scheme 1

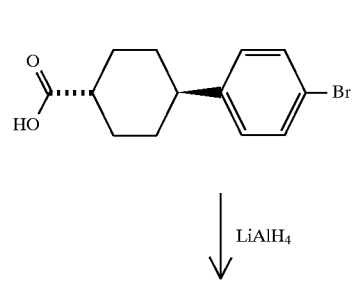

↓ LiAlH₄

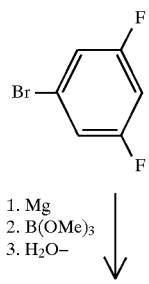

1. Mg
2. B(OMe)₃
3. H₂O—

↓

-continued
Scheme 1
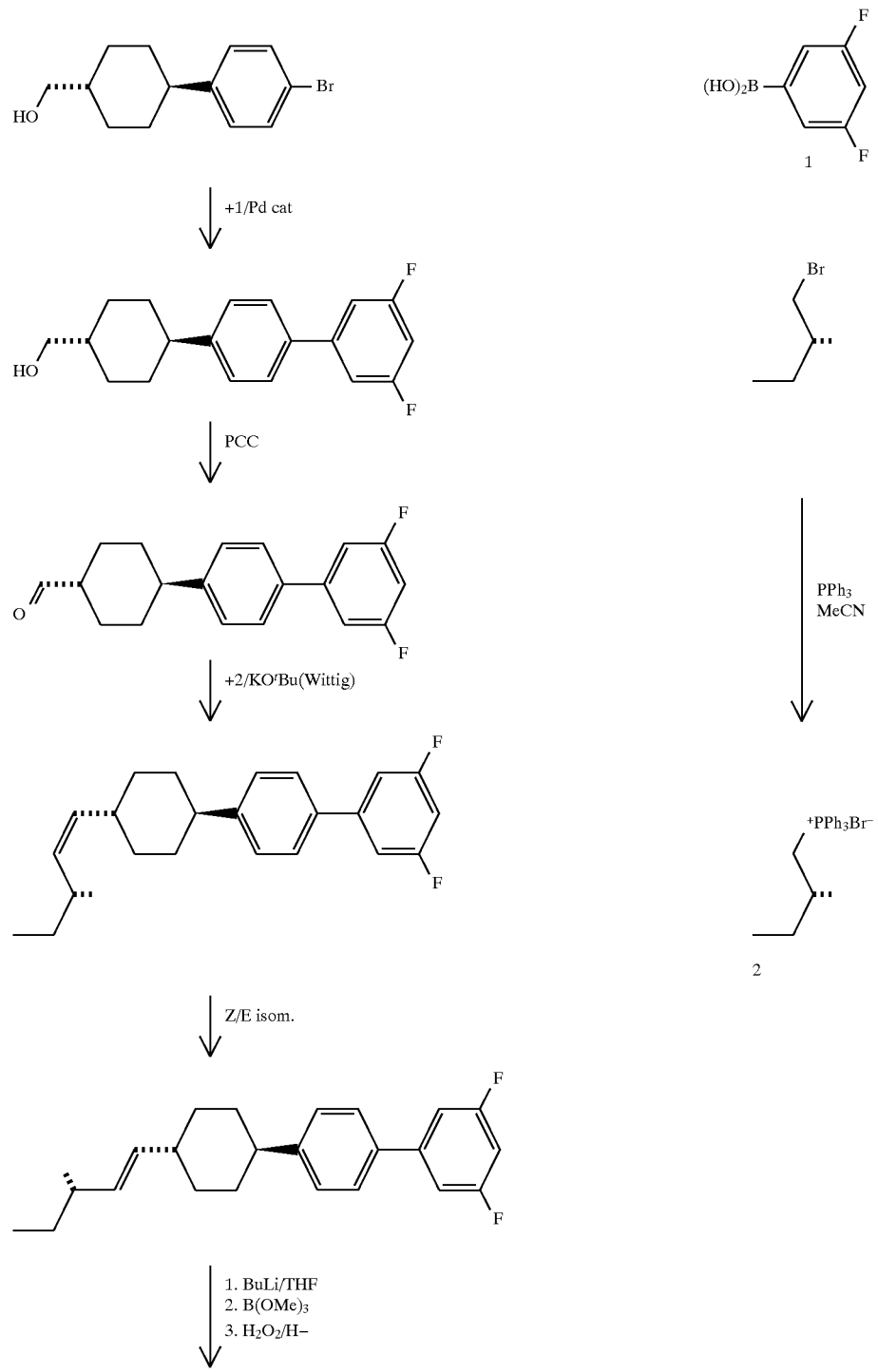

-continued
Scheme 1

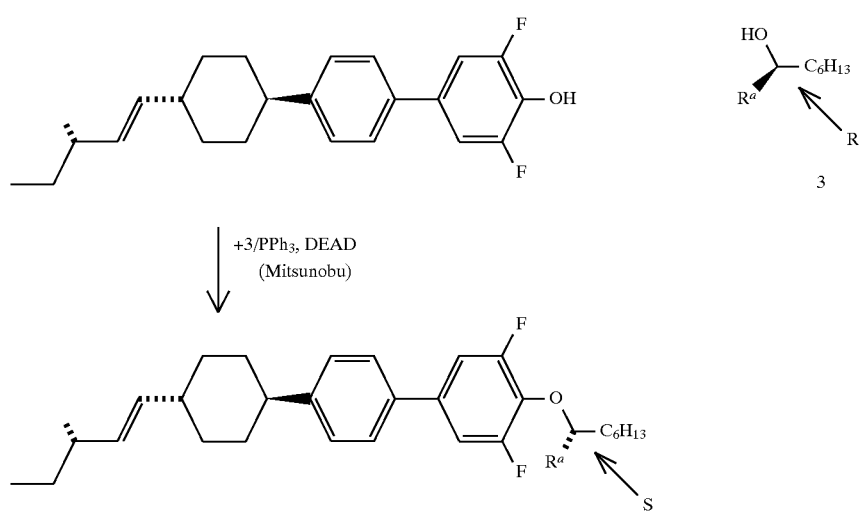

The novel media include at least one, preferably at least two, compounds of the formula I. The novel ferroelectric media preferably include an achiral smectic component S containing at least one achiral smectic compound, and a chiral component D is at least one chiral dope, where at least one chiral compound is a compound of the formula I. Particular preference is given to novel chiral tilted smectic liquid-crystalline phases whose achiral base mixture, besides compounds of the formula I, include at least one other component having negative or small positive dielectric anisotropy. The chirality is preferably based in part or in full on chiral compounds of the formula I. These phases preferably include one or two chiral compounds of the formula I. However, it is also possible to employ achiral compounds of the formula I (for example in the form of a racemate), in which case the chirality of the phase is due to other optically active compounds. If chiral compounds of the formula I are used, mixtures having an enantiomeric excess are also suitable in addition to the pure optical antipodes. The abovementioned further component(s) of the achiral base mixture can make up from 1 to 50%, preferably from 10 to 25%, of the base mixture.

The compounds of the formula I are particularly suitable as components of nematic liquid-crystalline phases, for example for preventing reverse twist.

In particular, the compounds of the formula I can be used as dopes for nematic liquid-crystalline phases for STN and active-matrix displays, where they are particularly distinguished by high helical twisting power (HTP) and high voltage holding ratios. In particular, doped, nematic mixtures of this type can easily be purified by treatment with aluminum oxide, in which case no or virtually no loss of chiral dope occurs. The media have small temperature dependences of the HTP.

Further advantages of using compounds of the formula I in novel liquid-crystalline media are their good compatibility with the nematic liquid crystals, which results in only very small changes, or none at all, in the clearing point of the liquid-crystal mixtures when the compounds of the formula I are employed in conventional amounts. The compounds of the formula I are also distinguished by very good solubility in the liquid-crystal media, in particular in those for AMD applications. The compounds of the formula I are thus also particularly suitable for AMD TN displays having high d/P values and improved grey shade display, as described in DE-A 42 12 744.

In the case of a positive temperature dependence of the HTP, i.e. decreasing pitch with increasing temperature, in particular at values in the range from 0.05%/° C. to 0.1%/° C. or more, the compounds of the formula I are also suitable in novel liquid-crystalline media for temperature compensation of the threshold voltage and thus on the operating voltage of TN and STN displays. Particular preference here is given to TN displays.

In addition, the compounds are particularly suitable for use in guest-host displays having a small cholesteric pitch, for example of the phase-change type.

A further preferred application of the compounds of the formula I is in ferroelectric liquid-crystal mixtures. Here, the compounds are suitable both for inducing spontaneous polarization and for compensating the pitch.

Furthermore, the novel chiral benzene derivatives can be used to prepare liquid-crystalline media for phase-change displays (for example Y. Yabe et al., SID 1991 Digest 261–264).

These novel liquid-crystalline media consist of, for example, from 2 to 25, preferably from 3 to 15, components, including at least one compound of the formula I. The other constituents are preferably selected from smectic or smectogenic substances, in particular known substances from the classes consisting of the azoxybenzenes, benzylideneanilines, biphenyls, terphenyls, phenyl- and cyclohexylbenzoates, phenyl and cyclohexyl cyclohexanecarboxylates, phenylcyclohexanes, cyclohexylbiphenyls, cyclohexylcyclohexanes, cyclohexylnaphthalenes, 1,4-biscyclohexylbenzenes, 4,4'-biscyclohexylbiphenyls, phenyl- and cyclohexylpyrimidines, phenyl- and cyclohexylpyridazines and N-oxides thereof, phenyl- and cyclohexyldioxanes, phenyl- and cyclohexyl-1, 3-dithianes, 1,2-diphenylethanes, 1,2-dicyclohexylethanes, 1-phenyl-2-cyclohexylethanes, optionally halogenated stilbenes, benzylphenyl ethers, tolans and substituted cinnamic acids. The liquid-crystalline mixture is based on the achiral compounds of this type.

The most important compounds which are suitable as constituents of liquid-crystalline phases of this type can be characterized by the formula I'

R-L-G-E-R'                    I' in which L and E are each a carbocyclic or heterocyclic ring system from the group consisting of 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, di- and tetrahydronaphthalene, quinazoline and tetrahydroquinazoline, G is —CH=CH—  —N(O)N—
—CH=CY—  —CH=N(O)—
—C≡C—  —CH$_2$—CH$_2$—
—CO—O—  —CH$_2$—O—
—CO—S—  —CH$_2$—S—
—CH=N—  —COO—Phe—COO— or a C—C single bond;

Y is halogen, preferably chlorine, or —CN, and

R and R' are alkyl, alkoxy, alkanoyloxy, alkoxycarbonyl or alkoxycarbonyloxy having 1 to 18, preferably 5 to 12, carbon atoms, or one of these radicals is alternatively, F, —CF$_3$, —OCF$_3$ or CN.

In most of these compounds, R and R' are each alkyl or alkoxy groups having different chain lengths, where the total number of carbon atoms in nematic media is generally from 2 to 9, preferably from 2 to 5, while in contrast the total number of carbon atoms in ferroelectric media is generally 12 or greater, preferably from 12 to 20, in particular from 13 to 18. However, other variants of the proposed substituents are also customary. Many such substances or mixtures thereof are commercially available. All these substances are obtainable by methods known from the literature.

The novel media comprise preferably 0.01–20%, more preferably 0.1–10%, in particular 0.2–5%, of one or more compounds of the formula I.

Preferred mixture components for ferroelectric media are compounds of the following formulae:

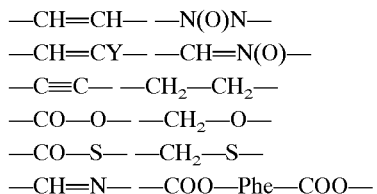

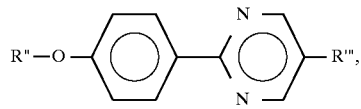

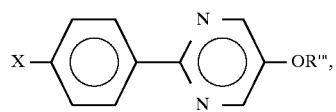

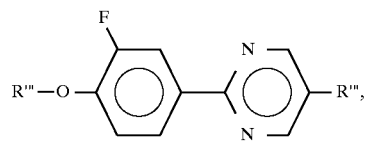

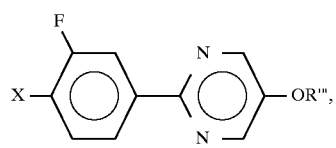

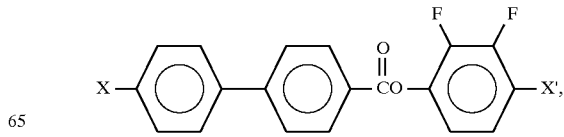

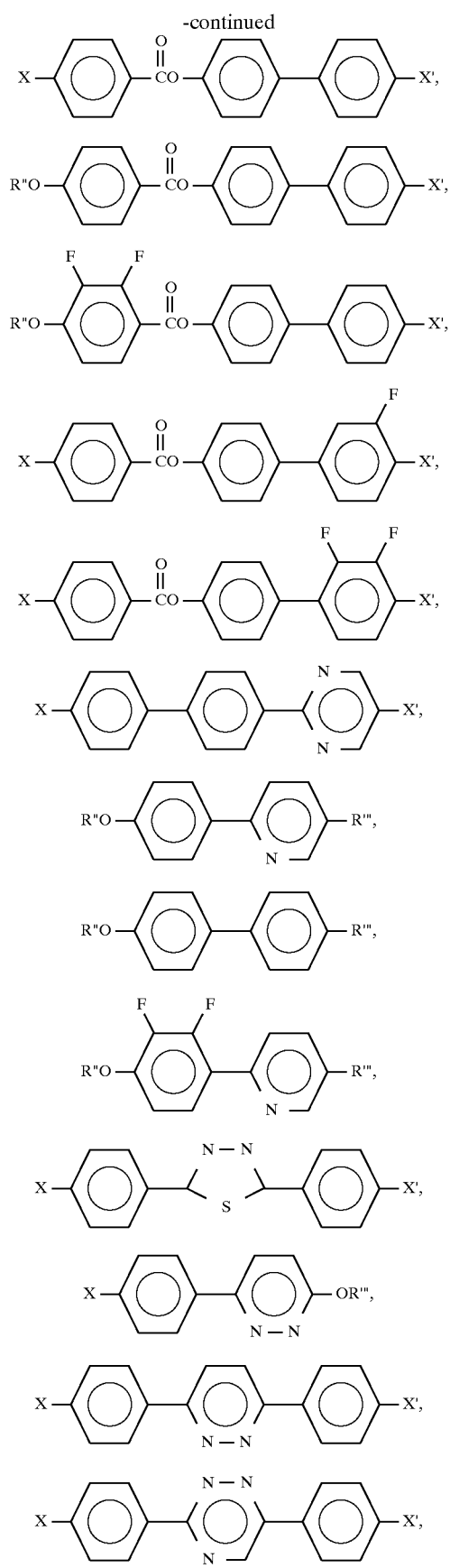
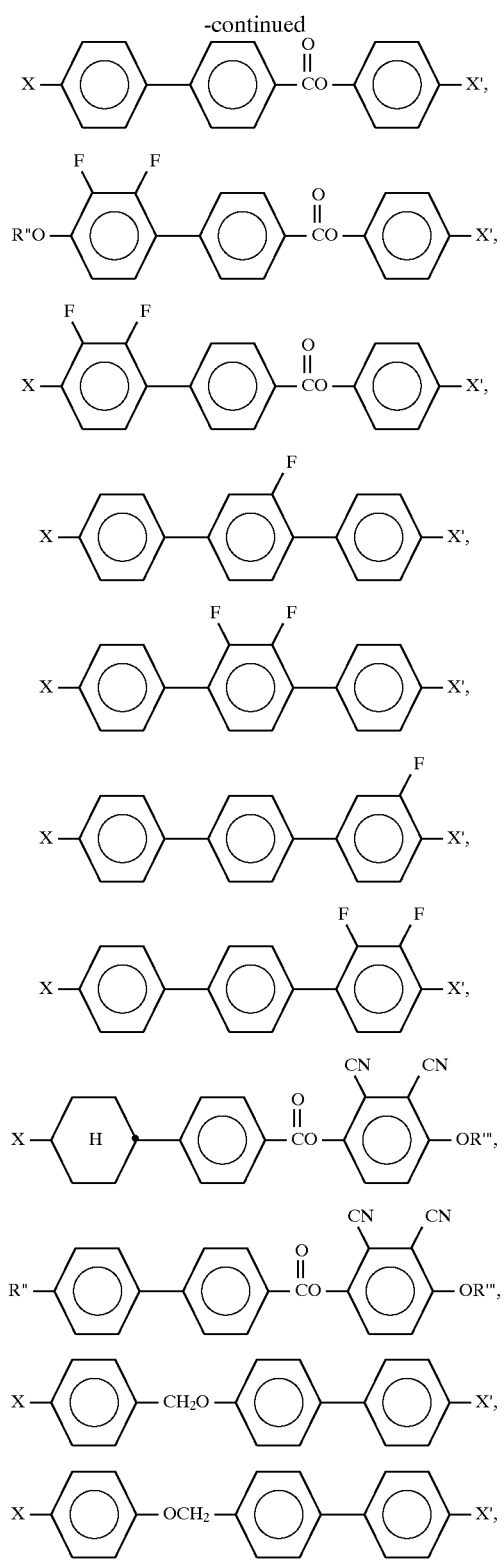

in which R'' and R''' are each, independently of one another, alkyl having 5 to 18 carbon atoms, and X and X' are each, independently of one another, alkyl, alkoxy, polyfluoroalkyl or polyfluoroalkoxy having 5 to 18 carbon atoms.

The novel phases are prepared in a manner conventional per se. In general, the components are dissolved in one another, expediently at elevated temperature.

By means of suitable additives, the liquid-crystalline phases can be modified in accordance with the invention in such a way that they can be used in all types of liquid-crystal display elements which have been disclosed hitherto, in particular of the SSFLC type in the chevron or bookshelf geometry.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application 195 42 849.8, filed Nov. 17, 1995, are hereby incorporated by reference.

The examples below are intended to illustrate the invention without representing a limitation. m.p.=melting point, c.p.=clearing point. Above and below, percentages are percent by weight; all temperatures are given in degrees Celsius. "Conventional work-up" means that water is added, the mixture is extracted with dichloromethane, the organic phase is separated off, dried and evaporated, and the product is purified by crystallization and/or chromatography.

In the present application and in the examples below, the structures of the liquid-crystal compounds are indicated by means of acronyms, the transformation into chemical formulae taking place in accordance with Tables A and B below. All radicals $C_nH_{2n+1}$ are straight-chain alkyl radicals having n carbon atoms. The coding in Table B is self-evident. In Table A, only the acronym for the parent structure is given. In individual cases, the acronym for the parent structure is followed, separated by a dash, by a code for the substituents $R^1$, $R^2$, $L^1$, $L^2$ and $L^3$;

| Code for $R^1$, $R^2$, $L^1$, $L^2$, $L^3$ | $R^1$ | $R^2$ | $L^1$ | $L^2$ | $L^3$ |
| --- | --- | --- | --- | --- | --- |
| nm | $C_nH_{2n+1}$ | $C_mH_{2m+1}$ | H | H | H |
| nOm | $C_nH_{2n+1}$ | $OC_mH_{2m+1}$ | H | H | H |
| nO.m | $OC_nH_{2n+1}$ | $C_mH_{2m+1}$ | H | H | H |
| n | $C_nH_{2n+1}$ | CN | H | H | H |
| nN.F | $C_nH_{2n+1}$ | CN | H | F | H |
| nF | $C_nH_{2n+1}$ | F | H | H | H |
| nOF | $OC_nH_{2n+1}$ | F | H | H | H |
| nCl | $C_nH_{2n+1}$ | Cl | H | H | H |
| nF.F | $C_nH_{2n+1}$ | F | H | F | H |
| nOmFF | $C_nH_{2n+1}$ | $OC_mH_{2m+1}$ | F | F | H |
| nmF | $C_nH_{2n+1}$ | $C_mH_{2m+1}$ | F | H | H |
| nCF$_3$ | $C_nH_{2n+1}$ | CF$_3$ | H | H | H |
| nOCF$_3$ | $C_nH_{2n+1}$ | OCF$_3$ | H | H | H |
| nOCF$_2$ | $C_nH_{2n+1}$ | OCHF$_2$ | H | H | H |
| nOCF$_2$.F.F | $C_nH_{2n+1}$ | OCHF$_2$ | H | F | F |
| nOCF$_2$.F | $C_nH_{2n+1}$ | OCHF$_2$ | H | F | H |
| nS | $C_nH_{2n+1}$ | NCS | H | H | H |
| rVsN | $C_rH_{2r+1}$—CH=CH—$C_sH_{2s}$ | CN | H | H | H |
| rEsN | $C_rH_{2r+1}$—O—$C_sH_{2s}$ | CN | H | H | H |
| nNF | $C_nH_{2n+1}$ | CN | F | H | H |
| nAm | $C_nH_{2n+1}$ | COOC$_m$H$_{2m+1}$ | H | H | H |
| nF.F.F | $C_nH_{2n+1}$ | F | H | F | F |
| nOCF$_3$.F | $C_nH_{2n+1}$ | OCF$_3$ | H | F | H |
| nOCF$_3$.F.F | $C_nH_{2n+1}$ | OCF$_3$ | H | F | F |
| nCl.F | $C_nH_{2n+1}$ | Cl | H | F | H |
| nCl.F.F | $C_nH_{2n+1}$ | Cl | H | F | F |

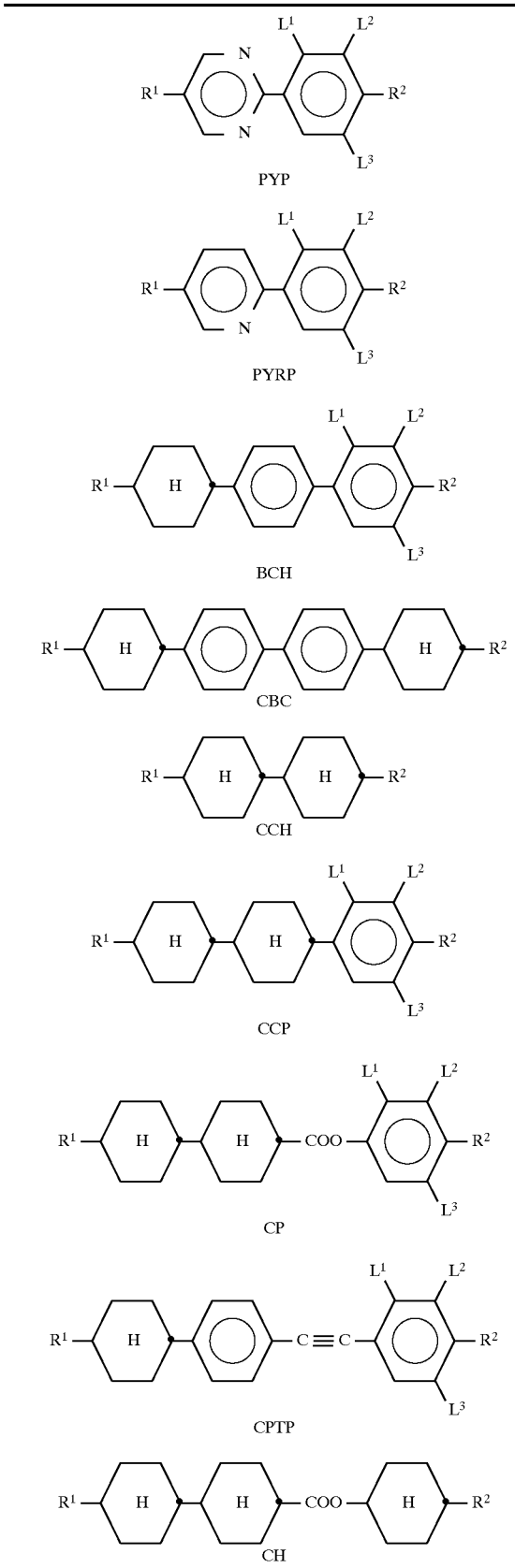

TABLE A

PYP

PYRP

BCH

CBC

CCH

CCP

CP

CPTP

CH

TABLE A-continued
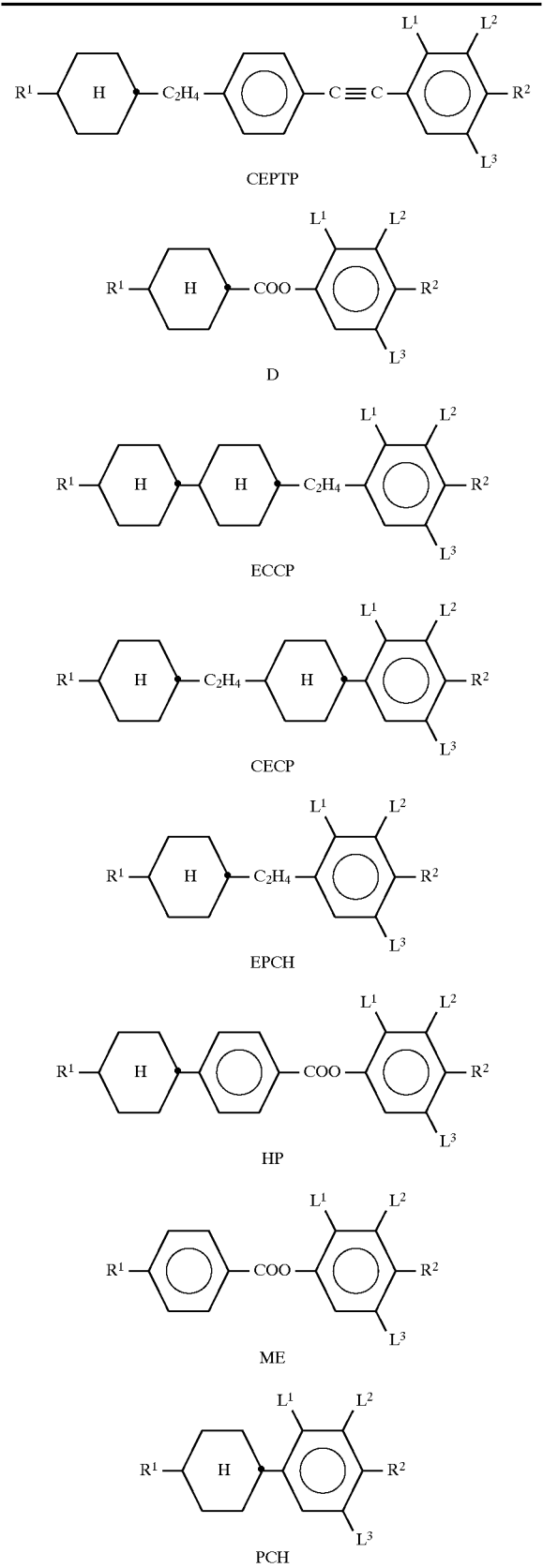
TABLE A-continued
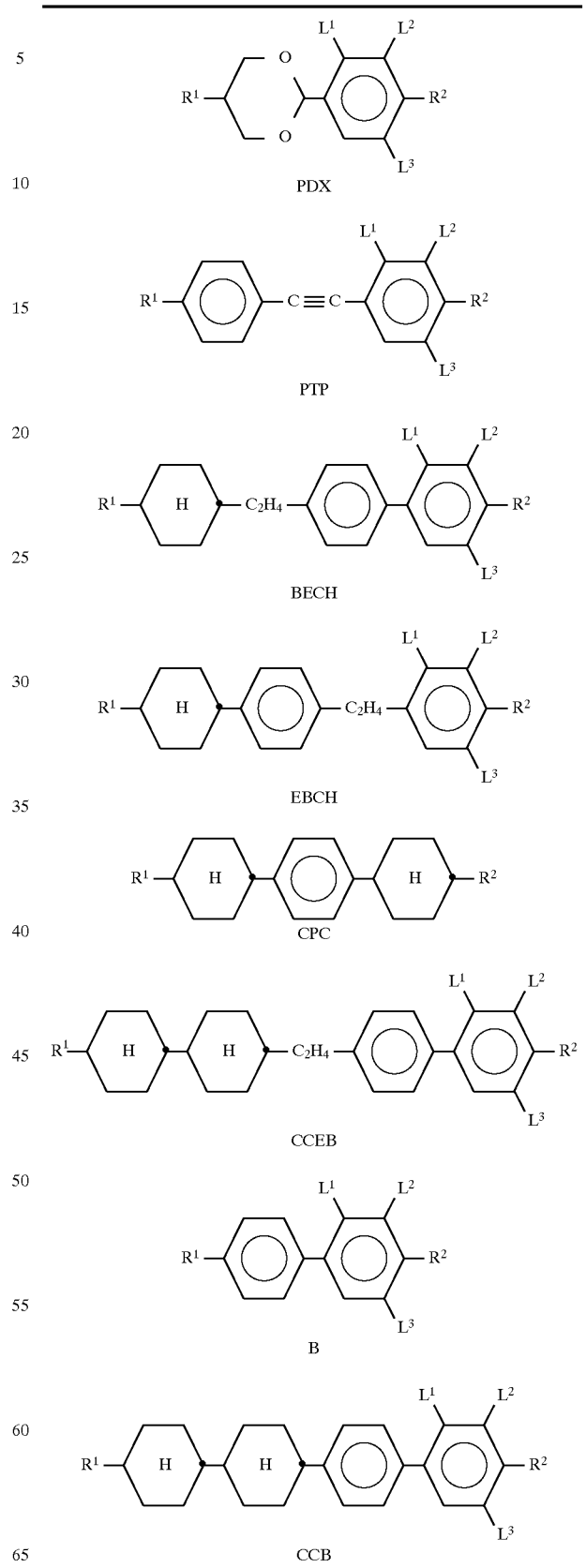

TABLE A-continued

CCB-n.FR²

B-n.FR²

CGP

CUP

CEUP

TABLE B

T3n

K3n

M3n

BCH-n.FX

Inm

TABLE B-continued

C-nm

C15

CB15

CBC-nmF

CCN-nm

CCPC-nm

CH-nm

HD-nm

HH-nm

NCB

Os-nm

CHE-2

ECBC-nm

ECCH-nm

CCH-n1EM

CCP-n08*.F.F

TABLE B-continued

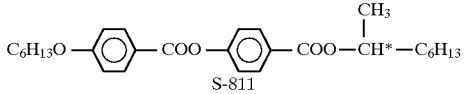

Furthermore, the following abbreviations are used:
C: Crystalline solid state,
S: Smectic phase (the index denotes the phase type, for example S=amectic C, SA=smectic A).
N: Nematic state,
Ch: Cholesteric phase,
I: Isotropic phase.
The number between two symbols indicates the conversion temperature in degrees Celsius.

The following abbreviations are used:
LiAlH$_4$ Lithium aluminum hydride
PCC Pyridinium chlorochromate
KOtBu Potassium tert-butoxide
BuLi Butyllithium
THF Tetrahydrofuran
B(OMe)$_3$ Trimethyl borate
PPh$_3$ Triphenylphosphine
DEAD Diethyl azodicarboxylate
MeCN Acetonitrile

EXAMPLES

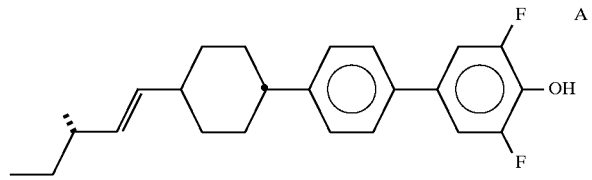

Example 1

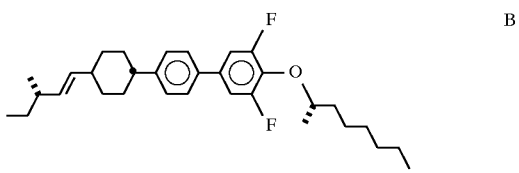

4.4 g of diisopropyl azodicarboxylate are added dropwise over the course of about 15 minutes at room temperature (about 20° C.) under nitrogen to a mixture of 7.8 g of compound A (prepared as shown in Scheme 1), 2.9 g of R-(−)-2-octanol, 5.7 g of triphenylphosphine and 80 ml of THF. The temperature does not exceed 25° C. during this addition. After the mixture has been stirred at room temperature for 3 hours, it is subjected to conventional work-up. Chromatography gives the compound B, abbreviated to CPU-4*V-08*, of melting point −15° C. HTP=11.1 μm$^{-1}$ (20° C., mixture B)

$[\alpha]_D^{20}$ (specific optical rotation at 20° C. for the D (sodium) line)=−13.70 (c=1% by weight, ethanol)

Example 2

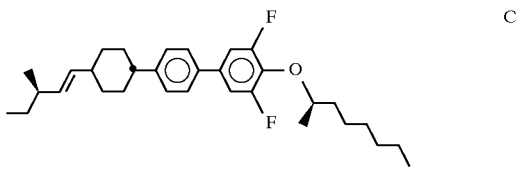

Compound C of melting point −14.5° C. is prepared analogously.

HTP=−11.0 μm$^{-1}$ (20° C. mixture B)
$[\alpha]_D^{20}$=+13.50 (c=1% by weight, ethanol)

Examples 3–29

Both the (S, S) and (R, R) forms of

*―CH=CH―[cyclohexyl]―A―[2,6-difluorophenyl]―O―(CH$_2$)$_r$―CH(X)―C$_m$H$_{2m+1}$ are prepared analogously

| A | r | X | m |
|---|---|---|---|
| cyclohexyl | 0 | CH$_3$ | 5 |
| cyclohexyl | 0 | CH$_3$ | 6 |
| cyclohexyl | 0 | CH$_3$ | 7 |
| cyclohexyl | 0 | C$_2$H$_5$ | 5 |
| cyclohexyl | 0 | C$_2$H$_5$ | 6 |
| cyclohexyl | 0 | C$_2$H$_5$ | 7 |
| cyclohexyl | 0 | n-C$_3$H$_7$ | 5 |
| cyclohexyl | 0 | n-C$_3$H$_7$ | 6 |
| cyclohexyl | 0 | n-C$_3$H$_7$ | 7 |
| cyclohexyl | 0 | n-C$_4$H$_9$ | 6 |
| cyclohexyl | 0 | n-C$_5$H$_{11}$ | 6 |
| cyclohexyl | 1 | F | 5 |
| cyclohexyl | 1 | F | 6 |
| cyclohexyl | 1 | F | 7 |
| phenyl | 0 | CH$_3$ | 5 |
| phenyl | 0 | CH$_3$ | 7 |
| phenyl | 0 | C$_2$H$_5$ | 5 |
| phenyl | 0 | C$_2$H$_5$ | 6 |
| phenyl | 0 | C$_2$H$_5$ | 7 |
| phenyl | 0 | n-C$_3$H$_7$ | 5 |

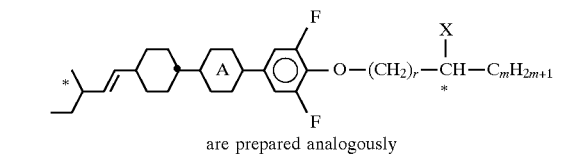

are prepared analogously

| A | r | X | m |
|---|---|---|---|
| phenyl | 0 | n-C$_3$H$_7$ | 6 |
| phenyl | 0 | n-C$_3$H$_7$ | 7 |
| phenyl | 0 | n-C$_4$H$_9$ | 6 |
| phenyl | 0 | n-C$_5$H$_{11}$ | 6 |
| phenyl | 1 | F | 5 |
| phenyl | 1 | F | 6 |
| phenyl | 1 | F | 7 |

Examples 30 and 31 (use)

1% by weight of compound B are dissolved in each of liquid-crystal mixtures A and B.

Composition of mixture A

| Substance | % by weight |
|---|---|
| ME2N.F | 2.00 |
| ME3N.F | 2.00 |
| ME5N.F | 4.00 |
| PYP-5F | 10.00 |
| CCH-301 | 10.00 |
| CCH-303 | 9.00 |
| PCH-301 | 16.00 |
| CH-33 | 4.00 |
| CH-35 | 4.00 |
| CH-43 | 4.00 |
| CH-45 | 4.00 |
| CP-33F | 8.00 |
| CP-35F | 8.00 |
| CCPC-33 | 5.00 |
| CCPC-34 | 5.00 |
| CCPC-35 | 5.00 |

Properties of mixture A
T(S-N)<−40° C.
Clearing point T (N,I)=103° C.
Viscosity (20° C.)=20 mm$^2$s$^{-1}$
Dielectric anisotropy (1 kHz, 20° C.)=4.0
Optical anisotropy (20° C., 589 rm)=0.0880
Composition of mixture B

| Substance | % by weight |
|---|---|
| PCH-7F | 8.5 |
| CCP-20CF$_3$ | 7.2 |

-continued

| Substance | % by weight |
|---|---|
| CCP-30CF$_3$ | 6.1 |
| CCP-40CF$_3$ | 5.7 |
| CCP-50CF$_3$ | 5.7 |
| ECCP-3F.F | 5.2 |
| ECCP-5F.F | 5.2 |
| ECCP-3F | 2.5 |
| CUP-3F.F | 3.2 |
| CUP-5F.F | 3.0 |
| CCP-20CF$_2$.F.F | 4.6 |
| CCP-30CF$_2$.F.F | 10.4 |
| CCP-50CF$_2$.F.F | 9.2 |
| CBC-33F | 3.6 |
| BCH-2F.F | 2.1 |
| BCH-3F.F | 2.7 |
| BCH-5F.F | 2.8 |
| BCH-32F | 1.8 |
| BCH-52F | 1.7 |
| PCH-301 | 5.0 |
| CCH-303 | 2.0 |
| CBC-53F | 1.8 |

Properties of mixture B
T(S-N)<-40° C.
Clearing point T (N,I)=98° C.
Optical anisotropy (20° C., 589 nm)=0.0952

The holding ratio (according to Jacob et al., "Physical Properties of LCs Voltage Holding Ratio", Merck Group LC Newsletter No. 9, October 1992) and the helical pitch (according to Grand-Jean Cano, as described in Hochgesand et al., "HTP of Chiral Dopants in Nematic LCs", Merck, October 1989) of the resultant doped mixtures are measured, and the HTP is calculated therefrom:

$$HTP=[c \cdot p]^{-1}$$

The resultant values are shown in Table I below:

TABLE I

| Mixture | A | B |
|---|---|---|
| Pitch as a function of temperature | | |
| Concentration (1) | 1% | 1% |
| T/°C.: | P/μm | P/μm |
| -7 | not measured | 8.93 |
| 0 | 11.6 | 8.86 |
| 20 | 11.6 | 8.97 |
| 50 | 11.8 | 9.39 |
| HTP as a function of temperature (HTP in μm$^{-1}$) | | |
| T/°C.: | HPT/μm$^{-1}$ | HTP/μm$^{-1}$ |
| -7 | not measured | 11.2 |
| 0 | 8.64 | 11.3 |
| 20 | 8.64 | 11.1 |
| 50 | 8.50 | 10.6 |
| HR (100° C.) | not measured | 99.5% |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A chiral benzene compound of the formula I

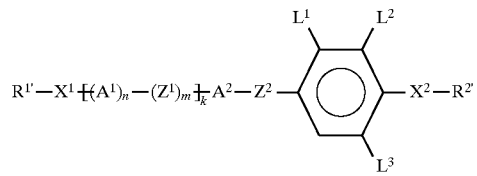

in which

L$^1$, L$^2$ and L$^3$ are each, independently of one another, F or H,

X$^1$ and X$^2$ are each, independently of one another, O or a single bond, R$^{1*}$ and R$^{2*}$ are each, independently of one another, a chiral radical containing at least one alkyl chain having 1 to 15 carbon atoms, in which one or more non-adjacent CH$_2$ groups are optionally replaced by O or CH=CH or both, and which is optionally substituted by F, Cl, CF$_3$, CF$_2$H, CFH$_2$ or CN, A$^1$ and A$^2$ are each, independently of one another, 1,4-phenylene which is unsubstituted or substituted by one or two fluorine atoms and in which, in addition, one or two CH groups are optionally replaced by N; or unsubstituted 1,4-cyclohexylene in which, in addition, one or two CH$_2$ groups are optionally replaced by O or S; or thiadiazole-2,5-diyl; or 1,4-bicyclo[2.2.2]octylene;

Z$^1$ and Z$^2$ are each, independently of one another, —COO—, —OCO—, —OCH$_2$—, —CH$_2$O—, —CH$_2$CH$_2$—, —CH=CH—, —C≡C— or a single bond, k is 0, 1 or 2, and n and m are each, independently of one another, 0 or 1 provided that:

(a) at least two of L$^1$, L$^2$ and L$^3$ is F, or (b) at least one of the radicals R$^{1*}$ and R$^{2*}$ is a radical of the formula II

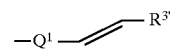

in which

Q$^1$ is a single bond or an alkylene group having 1 to 8 carbon atoms in which, in addition, one, two or more CH$_2$ groups are optionally replaced by —O— in such a way that two heteroatoms are not adjacent, and R$^{3*}$ is a chiral radical containing at least one alkyl chain having 1 to 15 carbon atoms, in which one or more non-adjacent CH$_2$ groups are optionally replaced by O or CH=CH or both, and which is optionally substituted by F, Cl, CF$_3$, CF$_2$H, CFH$_2$ or CN.

2. A chiral benzene compound according to claim 1, wherein at least one of the radicals R$^{1*}$ and R$^{2*}$ is a radical of the formula II

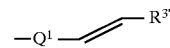

in which

Q$^1$ is a single bond or an alkylene group having 1 to 8 carbon atoms in which, in addition, one, two or more CH$_2$ groups are optionally replaced by —O— in such a way that two heteroatoms are not adjacent, and R$^{3*}$ is a chiral radical containing at least one alkyl chain having 1 to 15 carbon atoms, in which one or more non-adjacent CH$_2$ groups are optionally replaced by O or CH=CH or both and which is optionally substituted by F, Cl, CF$_3$, CF$_2$H, CFH$_2$ or CN.

3. A chiral benzene compound according to claim 1, wherein R$^{2*}$ is a radical of the formula III

   III in which

Q$^1$ is a single bond or an alkylene group having 1 to 8 carbon atoms in which, in addition, one, two or more CH$_2$ groups are optionally replaced by —O— in such a way that two heteroatoms are not adjacent, and R$^{3*}$ is a chiral radical containing at least one alkyl chain having 1 to 15 carbon atoms, in which one or more non-adjacent CH$_2$ groups are optionally replaced by O or CH=CH or both, and which is optionally substituted by F, Cl, CF$_3$, CF$_2$H, CFH$_2$ or CN.

4. A chiral benzene compound according to claim 2, wherein R$^{3*}$ is a chiral radical of the formula IV

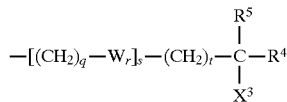   IV in which

W is CH=CH or O,

X$^3$ is H, CH$_3$, F, Cl, CF$_3$, CF$_2$H, CFH$_2$ or CN,

R$^4$ is H or an alkyl radical having 1 to 8 carbon atoms which is different from X$^3$ and in which one, two or more CH$_2$ groups are optionally replaced by —O— and/or by CH=CH in such a way that no two O atoms are adjacent, R$^5$ is an alkyl radical having 1 to 8 carbon atoms which is different from X$^3$ and R$^4$ and in which one or more CH$_2$ groups are optionally replaced, independently of one another, by —O— and/or CH=CH in such a way that no two O atoms are adjacent, s is from 0 to 4, r is 0 or 1, q is from 0 to 8, and t is from 0 to 8, where the sum of q, r and t is between 0 and 16.

5. A chiral benzene compound according to claim 3, wherein R$^{3*}$ is a chiral radical of the formula IV

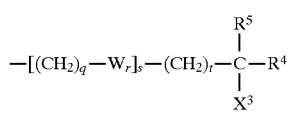   IV in which

W is CH=CH or O,

X$^3$ is H, CH$_3$, F, Cl, CF$_3$, CF$_2$H, CFH$_2$ or CN,

R$^4$ is H or an alkyl radical having 1 to 8 carbon atoms which is different from X$^3$ and in which one, two or more CH$_2$ groups are optionally replaced by —O— and/or by CH=CH in such a way that no two O atoms are adjacent, R$^5$ is an alkyl radical having 1 to 8 carbon atoms which is different from X$^3$ and R$^4$ and in which one or more CH$_2$ groups are optionally replaced, independently of one another, by —O— and/or CH=CH in such a way that no two O atoms are adjacent, s is from 0 to 4, r is 0 or 1, q is from 0 to 8, and t is from 0 to 8, where the sum of q, r and t is between 0 and 16.

6. A chiral benzene compound according to claim 1, wherein R$^{1*}$ is a radical of the formula (3)

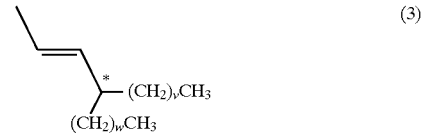   (3)

in which v and w are each, independently of one another, from 0 to 7, but v is not equal to w.

7. A chiral benzene compound according to claim 1 of the formula I1

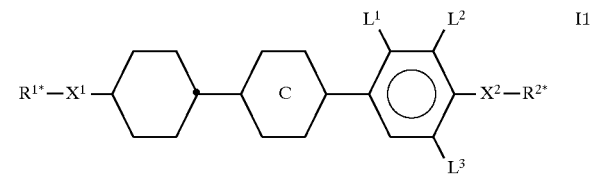   I1 where

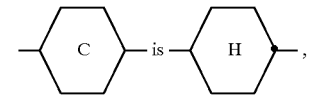

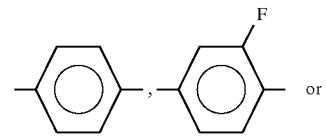   or

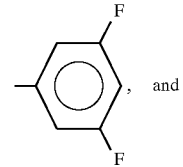   and

R$^{1*}$, X$^1$, L$^1$, L$^2$, L$^3$, X$^2$ and R$^{2*}$ are as defined.

8. A chiral benzene compound according to claim 1, in which L$^1$ is H and at least one of L$^2$ and L$^3$ are F.

9. A chiral benzene compound of claim 1 of the formula

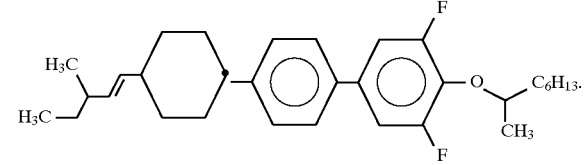

10. A chiral benzene compound according to claim 1, wherein the two chiral groups R$^{1*}$ and R$^{2*}$ have the same absolute configuration.

11. A liquid-crystalline medium comprising at least one chiral benzene derivative of the formula I according to claim 1.

12. The liquid-crystalline medium according to claim 11, wherein the total concentration of the chiral benzene compound of formula I is from 0.01% by weight to 20% by weight.

13. A liquid-crystalline medium according to claim 12 which exhibits a temperature dependence of the cholesteric pitch in the range from 0° C. to 50° C. of at most 0.1%/° C.

14. An electrooptical display containing a liquid-crystalline medium according to claim 13.

15. A supertwist liquid-crystal display comprising a liquid-crystal mixture which includes at least one chiral benzene compound of the formula I of claim 1.

16. An active matrix liquid-crystal display comprising a liquid-crystal mixture which includes at least one chiral benzene compound of the formula I of claim 1.

17. A chiral benzene compound of claim 1, wherein each of $R^{1*}$ and $R^{2*}$ have at least one $CH_2$ group replaced by a $CH=CH$ group.

18. A chiral benzene compound of claim 1, wherein each or $Z^1$ and $Z^2$ are a single bond.

19. A chiral benzene compound of claim 1, wherein $L^1$ is H; $L^2$ and $L^3$ are F; k, m and n are each 1; $A^1$ and $A^2$ are each unsubstituted 1,4-cyclohexylene; and $Z^1$ and $Z^2$ are each a single bond.

* * * * *